United States Patent
Weeber

(10) Patent No.: US 10,448,819 B2
(45) Date of Patent: Oct. 22, 2019

(54) METHOD FOR DESIGNING, EVALUATING AND OPTIMIZING OPHTHALMIC LENSES AND LASER VISION CORRECTION

(71) Applicant: AMO Groningen B.V., Groningen (NL)

(72) Inventor: Hendrik A. Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 899 days.

(21) Appl. No.: 14/080,499

(22) Filed: Nov. 14, 2013

(65) Prior Publication Data
US 2014/0081395 A1 Mar. 20, 2014

Related U.S. Application Data

(62) Division of application No. 13/297,103, filed on Nov. 15, 2011, now abandoned.

(60) Provisional application No. 61/418,234, filed on Nov. 30, 2010.

(51) Int. Cl.
- *A61F 2/16* (2006.01)
- *G02C 7/02* (2006.01)
- *A61B 3/00* (2006.01)

(52) U.S. Cl.
CPC .......... *A61B 3/0025* (2013.01); *A61F 2/1613* (2013.01); *A61F 2/1637* (2013.01); *G02C 7/027* (2013.01); *G02C 2202/22* (2013.01)

(58) Field of Classification Search
None
See application file for complete search history.

(56) References Cited

U.S. PATENT DOCUMENTS

| | | | |
|---|---|---|---|
| 6,609,793 B2 | 8/2003 | Norrby et al. | |
| 2003/0033013 A1 | 2/2003 | Callahan et al. | |
| 2006/0203198 A1 | 9/2006 | Liang | |
| 2006/0244906 A1 | 11/2006 | Piers et al. | |
| 2006/0279699 A1* | 12/2006 | Liang ................... | A61B 3/1015 351/246 |
| 2006/0279700 A1 | 12/2006 | Liang | |
| 2008/0033546 A1 | 2/2008 | Liang | |
| 2009/0000628 A1* | 1/2009 | Somani ................... | A61F 9/00 128/898 |
| 2010/0097569 A1 | 4/2010 | Weeber et al. | |

FOREIGN PATENT DOCUMENTS

| | | |
|---|---|---|
| WO | WO-0189424 A1 | 11/2001 |
| WO | WO-02074210 A2 | 9/2002 |

(Continued)

OTHER PUBLICATIONS

Weeber, et al, "Population-based visual acuity in the presence of defocus well predicted by classical theory", JBO Letters, 2010, 15(4):040509-1.*

(Continued)

*Primary Examiner* — Leslie Lopez
(74) *Attorney, Agent, or Firm* — Johnson & Johnson Surgical Vision, Inc.

(57) ABSTRACT

The present invention relates generally to lens design and, more particularly, to a method for designing, evaluating and optimizing ophthalmic lenses and laser vision correction in order to optimally manage issues resulting from, or related to, halos.

9 Claims, 5 Drawing Sheets

(56) References Cited

FOREIGN PATENT DOCUMENTS

| WO | WO 2007/142981 A2 * | 12/2007 | ............... G02C 7/02 |
| WO | WO-2007142981 A2 | 12/2007 | |

OTHER PUBLICATIONS

Jendritza, et al (Jendritza) ("Wavefront-guided Excimer Laser Vision Correction After Multifocal IOL Implantation", J of Refractive Surgery, v24 (Mar. 2008), pp. 274-279) (Year: 2008).*

Weeber, et al (Weeber) ("Population-based Visual Acuity in the Presence of Defocus Well Predicted by Classical Theory", JBO Letters, v28(1) (2010), pp. 040509-1-040509-3) (Year: 2010).*

Fernandez E.J., et al., "Adaptive Optics Visual Simulator," Journal of Refractive Surgery, 2002, vol. 18 (5), pp. S634-S638.

Guirao A., et al., "Corneal Wave Aberration from Videokeratography: Accuracy and Limitations of the Procedure," Journal of the Optical Society of America, 2000, vol. 17 (6), pp. 955-965.

International Search Report and Written Opinion for Application No. PCT/US2011/060842, dated Feb. 8, 2012, 18 pages.

Weeber H.A., et al., "Influence of Corneal Aberrations on Dysphotopsia with Multifocal IOLs," ARVO, 2011, Abstract.

Weeber H.A., et al., "Influence of Corneal Aberrations on Dysphotopsia with Multifocal IOLs," RD3115, 2011.

Weeber H.A., et al., "Optical and Visual Performance of Patient Populations Implanted with Monofocal and Multifocal IOLs in the Presence of Defocus," Investigative Ophthalmology & Visual Science, 2010, vol. 51, E-Abstract 5751.

Weeber H.A., et al., "Population-based Visual Acuity in the Presence of Defocus Well Predicted by Classical Theory," Journal of Biomedical Optics, 2010, vol. 15 (4), pp. 040509.

Weeber H.A., et al., "Theoretical Performance of Intraocular Lenses Correcting Both Spherical and Chromatic Aberration," Journal of Refractive Surgery, 2012, vol. 28 (1), pp. 48-52.

Jendritza B.B., et al., "Wavefront-Guided Excimer Laser Vision Correction after Multifocal IOL Implantation," Journal of Refractive Surgery, Mar. 2008, vol. 24 (3), pp. 274-279.

* cited by examiner

METHOD FOR DESIGNING, EVALUATING AND OPTIMIZING OPHTHALMIC LENSES AND LASER VISION CORRECTION

The present application is a divisional application of U.S. application Ser. No. 13/297,103, filed on Nov. 15, 2011 under the same title, which claims priority under 35 U.S.C. § 119(e) to provisional application No. 61/418,234 filed on Nov. 30, 2010 under the same title, both of which are incorporated herein by reference in their entirety.

BACKGROUND OF THE INVENTION

Field of the Invention

The present invention relates generally to ophthalmic lenses and laser vision correction, and more particularly, to a method for designing, evaluating and optimizing ophthalmic lenses and laser vision correction in order to optimally manage issues resulting from, or related with, halos.

Description of the Background

Ophthalmic lenses, such as intraocular lenses (IOLs), phakic IOLs, piggyback IOLs, spectacle lenses, contact lenses, and corneal implants may be used to enhance or correct vision. For example, IOLs are routinely used to replace the crystalline lens of an eye during cataract surgery.

Ophthalmic lenses, such as IOLs may be monofocal or multifocal. A monofocal IOL provides a single focal point, whereas a multifocal IOL provides multiple focal points for correcting vision at different distances. For example, a bifocal IOL provides two different focal points, routinely one for near vision and one for distant vision.

Ophthalmic lenses, such as the aforementioned multifocal IOLs, may be refractive, diffractive, or both refractive and diffractive. Multifocal refractive IOLs may be comprised of several concentric annular optical zones with each zone providing for a near or a far focus. A diffractive multifocal IOL is generally divided into a plurality of annular zones, or echelettes, that are offset parallel to the optical axis by predetermined diffractive step heights in order to provide a specific phase relationship between the annular zones. A diffractive multifocal IOL may divide incident light into two diffractive orders to provide near and distant vision.

Although multifocal lenses are effective for vision correction, further enhancements would be advantageous. One problem associated with multifocal/bifocal IOLs, in part due to the typically bifocal configuration of the refractive/diffractive zones, is dysphotopsia, and in particular halos under low light conditions. Halos may arise when light from the unused focal image creates an out-of-focus image that is superimposed on the used focal image. For example, if light from a distant point source is imaged onto the retina by the distant focus of a bifocal IOL, the near focus of the IOL will simultaneously superimpose a defocused image on top of the image formed by the distant focus. This defocused image may manifest itself in the form of a ring of light surrounding the in-focus image, and is referred to as a halo. In addition to multifocality, add power and light distribution may also contribute to dysphotopsia.

Discomfort, visual disturbance or nuisance from dysphotopsia may be tied to personal attributes or habits. For example, a patient's psychological profile may play an important role; more critical patients may be more affected by halos than those less critical. In addition, habitual circumstances may influence discomfort, e.g. truck drivers are typically more affected by halos due to night driving.

Aberrations of the cornea and in particular higher order corneal aberrations have a direct impact on halos. Corneal topographic analysis using photokeratoscopic or videokeratographic methods provides objective measures of corneal topography. Current measurement devices typically employ several concentric rings or multiple discrete light sources to reflect a luminous object of known dimension from the cornea. The size of the cornea-reflected images of this object is then measured with photographic or electro-optical recording methods to compare the shape of the cornea with a theoretical spherical shape. If the cornea is spherical, for example, the reflected images of the ring-shaped objects will be equally spaced, continuous, concentric ring-shaped patterns. If the cornea has surface defects, or is not precisely spherical, the resultant ring images will be less equally spaced or will have a different shape, such as an elliptical shape.

Corneal topography can thus be used to determine the optical aberrations of the cornea. Such aberrations in conjunction with the designs, methods, and systems disclosed herein may be used to manage halos. And, based on the aforementioned, a need exists for a lens design and, more particularly, to an apparatus, system and method for designing, evaluating and optimizing ophthalmic lenses for such management.

SUMMARY OF THE INVENTION

The present invention is and includes an apparatus, system and method to design, evaluate and optimize ophthalmic lenses, such as IOLs. In addition, the apparatus, system and methods can be used to optimize a laser vision correction nomogram.

A method of optimizing, evaluating and/or designing an ophthalmic lens involves initially measuring the preoperative corneal aberrations of a patient. Then, a simulated halo image, with a multifocal IOL incorporated, may be calculated for the corneal aberrations; the simulated image determining the halo size, shape and intensity. A reference halo which demonstrates acceptable dysphotopsia may then be compared with the simulated halo. Based on the comparison, a decision may be made whether to implant the multifocal IOL.

Another preferred embodiment, involves the following steps: measuring the preoperative corneal aberrations of a patient (or group of patients); calculating a simulated halo image for these aberrations, with the multifocal IOL; determining the halo size, shape and intensity; having a reference halo which demonstrates acceptable dysphotopsia; optimizing the IOL aberration profile so as to result in minimal halo, specifically when combined with the patient's (or group of patients') corneal aberration profile; and implanting the custom multifocal IOL.

It is understood that an important aspect of certain embodiments of this invention includes the characterization of the corneal aberrations of a selected group of patients or population for expressing an average corneal aberration. Average corneal aberration terms of the population expressed, for example, as an average linear combination of polynomials can then be calculated and used in the lens design method.

In another preferred method, after a multifocal IOL is implanted, the corneal aberrations of a patient are measured. Then, a simulated halo image is calculated for these aberrations with the multifocal IOL; the simulated image revealing the halo size, shape and intensity. A reference halo which demonstrates acceptable dysphotopsia is then compared to the simulated halo. Based on the comparison a determination is made whether the halo is predominantly caused by the corneal aberrations. If it is, the corneal aberrations may be modified by laser vision correction to minimize the halos, and with that, minimize the discomfort caused by halos.

Another preferred embodiment, involves the following steps: measuring the preoperative corneal aberrations of the multifocal IOL patient; calculating a simulated halo image for these aberrations, with the multifocal IOL; determining the halo size, shape and intensity; having a reference halo which demonstrates acceptable dysphotopsia; optimizing the laser vision correction so as to result in minimal halo; applying the laser vision correction to the patient's cornea.

Another preferred embodiment, involves the following steps: measuring the preoperative corneal aberrations of the multifocal IOL patient; using a vision simulator, measure the patient's visual performance (e.g. halo size, shape and intensity; discomfort, contrast vision, visual acuity), while varying the patient's corneal aberration; based on the test, determining the optimal corneal aberration as to optimize the visual performance; applying a laser vision correction to generate the optimal corneal aberration onto the patient's cornea.

Another preferred embodiment, involves the following steps: optimizing a corneal correction (e.g. presby-lasik), the simulated halo image being one of the optimization parameters; applying the presby-laser vision correction to the patient's cornea. Prior to optimizing a corneal correction, one may measure the corneal aberrations of a patient suffering discomfort or reduced visual performance.

An exemplary ophthalmic lens would include an anterior surface and an opposing posterior surface wherein at least one of the surfaces of the ophthalmic lens is characterized by an equation including a first coefficient configured to shape the halo and intensity profile in order to minimize bother from the halo.

A preferred embodiment includes an ophthalmic lens wherein at least one of the surfaces is characterized by a phase profile configured to modify the wavefront aberration in order to shape the halo and intensity profile in order to minimize bother from the halo. The phase profile may modify spherical aberration, coma, trefoil, and/or the product of any combination.

Thus, the present invention provides a method for designing, evaluating and optimizing ophthalmic lenses and laser vision correction.

BRIEF DESCRIPTION OF THE DRAWINGS

Understanding of the disclosure will be facilitated by consideration of the following detailed description of the embodiments, taken in conjunction with the accompanying drawings, in which like numerals refer to like parts and in which.

DETAILED DESCRIPTION OF THE INVENTION

It is to be understood that the figures and descriptions of the present invention have been simplified to illustrate elements that are relevant for a clear understanding of the present invention, while eliminating, for the purposes of clarity, many other elements found in typical optical and optical simulation apparatuses, systems and methods. Those of ordinary skill in the art will recognize that other elements are desirable and/or required in order to implement the present invention. However, because such elements are well known in the art, and because they do not facilitate a better understanding of the present invention, a discussion of such elements is not provided herein.

Figure 1:
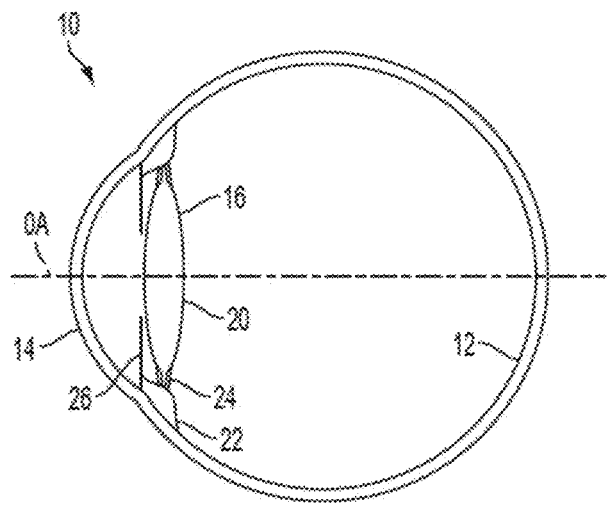
FIG. 1 is an illustration of an eye in the natural state.

FIG. 1 is an illustration of an eye 10 in the natural state. The eye 10 includes a retina 12 for receiving an image, produced by the cornea 14 and the natural lens 16, from light incident upon the eye. The natural lens 16 is disposed within a capsular bag 20. The iris 26 separates the anterior and posterior chambers of the eye and may operate to change the aperture, i.e. pupil size of the eye. More specifically, the diameter of the incoming light beam is controlled by the iris 26, which forms the aperture stop of the eye.

The capsular bag 20 is a resilient material that changes the shape and/or location of natural lens in response to ocular forces produced when the ciliary muscles 22 contract and stretch the natural lens 16 via the zonular fibers 24 disposed about an equatorial region of the capsular bag 20. This shape change may flatten the natural lens 16, thereby producing a relatively low optical power for providing distant vision in an emmetropic eye. To produce intermediate and/or near vision, the ciliary muscles 22 contract, thereby relieving tension on the zonular fibers 24. The resiliency of the capsular bag 16 thus provides an ocular force to reshape the natural lens 16 to modify the curvature to provide an optical power suitable for required vision. This change, or "accommodation," is achieved by changing the shape of the crystalline lens. Accommodation, as used herein, includes changing the focus of the eye for different distances.

Figure 2:
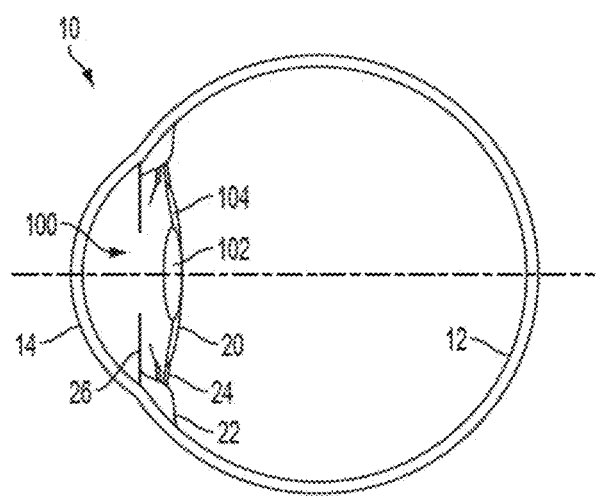
FIG. 2 is an illustration of an eye having an intraocular lens.

FIG. 2 illustrates an eye 10 having a natural lens replaced with an IOL 102. The natural lens may require removal due to a refractive lens exchange, or due to a disease such as cataracts, for example. Once removed, the natural lens may be replaced by an IOL 102 to provide improved vision in the eye. The IOL 102 may include an optic and haptics 104 or support structure for centering the optic. The haptics 104 may center the optic, and may transfer ocular forces from the ciliary muscle 22, zonules 24, and/or capsular bag 20 to the optic to change the shape, power, and/or axial location of the optic relative to the retina 12.

Figure 3:
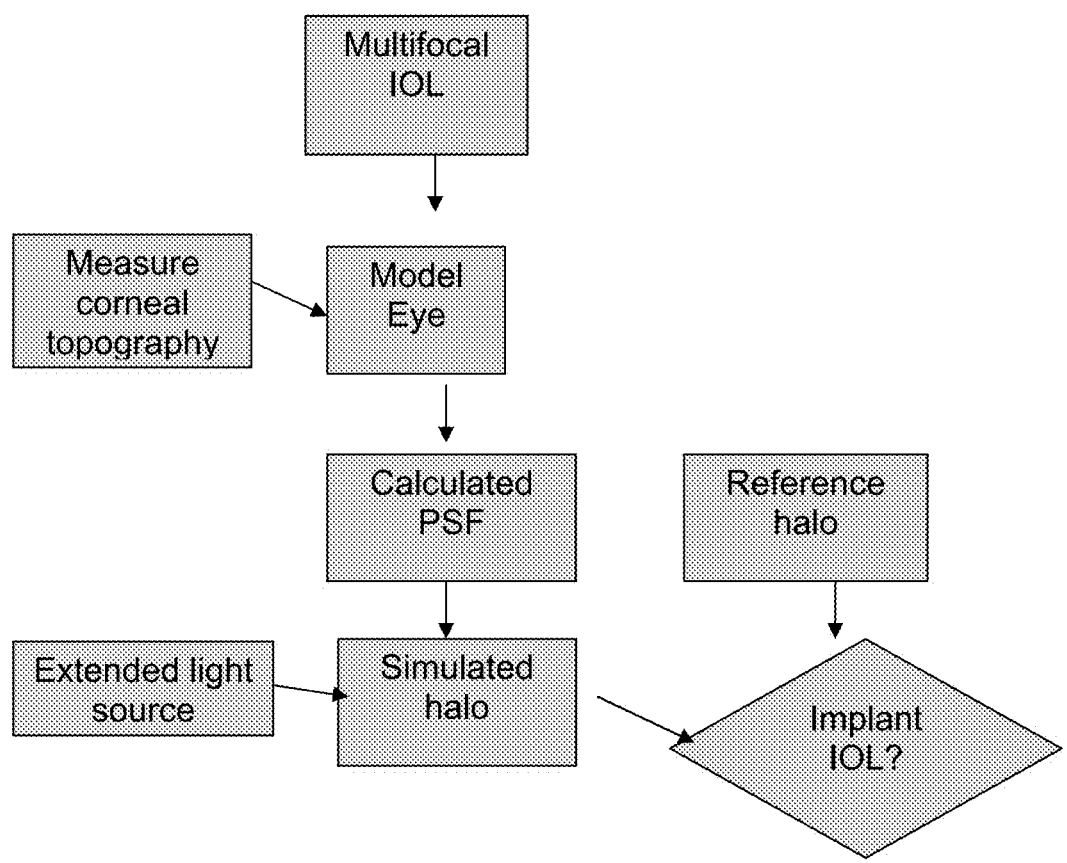
FIG. 3 is a flow diagram illustrating a method for optimizing an ophthalmic lens in accordance with the present invention.

FIG. 3 is a flow diagram illustrating methods of optimizing an ophthalmic lens, such as, for example, the IOL illustrated in FIG. 2, in accordance with the present invention. In the illustrated method, an ophthalmic lens may be designed and/or provided for modeling and for clinical application. With reference to FIG. 3, a method of optimizing, evaluating and/or designing an ophthalmic lens is comprised of measuring the preoperative corneal aberrations of the patient according to well-known topographical measurement methods. This may be done by taking the difference in optical path between the chief ray and a marginal ray over the pupil which yields the wavefront aberration for the cornea. (Guirao, A., & Artal, P. (2000). Corneal wave aberration from videokeratography: accuracy and limitations of the procedure. J Opt Soc Am A, 17 (6), 955-965.).

Alternatively, ray tracing can be performed, e.g. using general purpose optical design software (e.g. Code V, Zemax, OSLO).

Preferably, at least the front corneal surface is measured and more preferably both the front and rear corneal surfaces are measured and characterized together in resulting wavefront aberration terms, such as a linear combination of polynomials which represent the total corneal wavefront aberrations. In the art of optics, topographical processes may include mathematically modeling a surface of the cornea using polynomial expansion series techniques, e.g. Seidel or Zernike polynomials, or the wavefront aberration can be calculated over a grid of points over the pupil.

For normal healthy corneas, $5^{th}$ order Zernike expansion is typically sufficient to describe the corneal aberrations. The aberrations include both lower order terms, such as defocus and astigmatism, along with higher order terms, such as spherical aberration, coma, trefoil, etc., up to pentafoil. However, for non-uniform corneas, like post-LASIK corneas, more terms may be needed. For non-uniform corneas, it may be necessary to describe the corneal aberrations at discrete points on a grid filling the pupil.

The correlation between corneal aberrations and halo shape and intensity is demonstrated in the following example which encompasses the use of a set of 46 physiological eye models. The eye model (computer models) are based on the eyes of 46 cataract patients, and are described in further detail in the following which are incorporated herein by reference: Weeber, H. A., Featherstone, K. A., & Piers, P. A. (2010). Population-based visual acuity in the presence of defocus well predicted by classical theory. J. Biomedical Optics, 15 (4), 040509/040501-040509/040503; Weeber, H. A., & Piers, P. A. (2010). Optical and Visual Performance of Patient Populations Implanted With Monofocal and Multifocal IOLs in the Presence of Defocus. Invest. Ophthalmol. Vis. Sci., 51: E-Abstract 5751; Weeber, H. A., & Piers, P. A. (2011). Theoretical Performance of Intraocular Lenses correcting both Spherical and Chromatic Aberration. J. Refr. Surg., DOI: 10.3928/1081597X-20111103-01

The corneas of these eye models are described by 5th order Zernike sag surfaces, and the eye models have spectacle lenses in front of them. For this analysis, the eye models were 'implanted' with a diffractive multifocal IOL, having a pupil-independent diffractive profile across the entire optic, and a 50%:50% light distribution between far and near focus. However, it should be appreciated by those skilled in the art that any other multifocal lens would generate comparable analysis.

In addition to the set of physiological eyes, diffraction limited eyes were generated having the same corneal power, but generating no wavefront aberrations. These eye models served as reference models, being 'perfect' eyes.

All eye models have a physical pupil diameter of 4 mm which represents the pupil diameter of an average cataract patient under mesopic lighting conditions.

For both sets—the physiological eye models, and the corresponding diffraction limited eye models—polychromatic point spread functions (PSF) were calculated.

Figure 4:
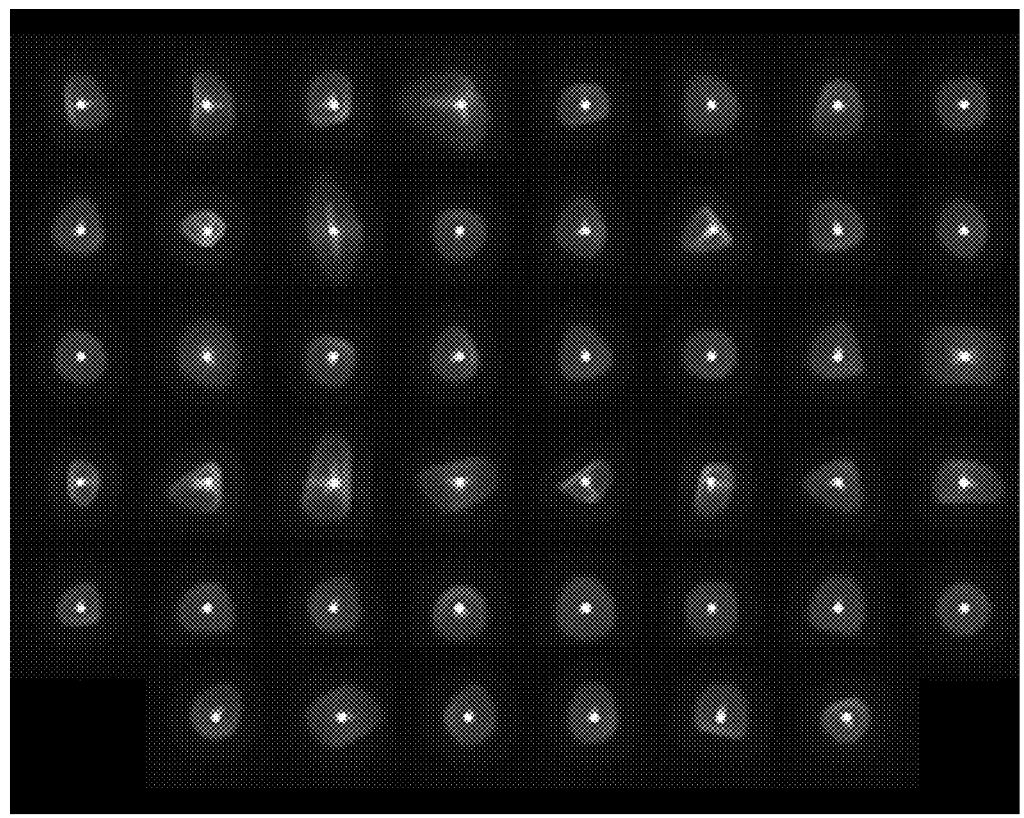
FIG. 4 illustrates the halo image of 46 physiological eyes as further detailed below.

Then, an extended source, representing a headlight of 15 cm diameter at a 100 m distance was convoluted with the PSF. This resulted in the retinal image of the headlight, furtheron referenced as 'halo images'. For optimal display and print, the pictures were processed using a gamma correction of 0.4. FIG. 4 shows the halo images of the 46 physiological eye which clearly demonstrates that the halo appearance differs considerably between the different eye models.

An assessment of the patient inconvenience from halos can be done in a variety of ways. One way is to determine the retinal image of halos in patients, and then assess the nuisance perceived by these patients (e.g. by a questionnaire). Alternatively (and as done in this example), the patient inconvenience from halo images can be estimated by assessment of the shape, area, brightness and contrast of the halo images. There are two additional ways to assess the halo image: by evaluating the halo image of the physiological eye, and by evaluating the difference between the halo image of the physiological eye and that of the diffraction limited eye. In the latter case, the halo image of the diffraction limited eye is subtracted from the halo image of the physiological eye. The resulting image ('delta image') highlights the halo only, without the central headlight.

These aspects are consolidated in the following metrics for halo patient inconvenience and corneal aberrations, the correlation between which are illustrated in Tables 1 and 2 below:

H1. (Image-)Correlation between the halo image of the physiological eye and the halo image of the diffraction limited eye. As the halo image of the diffraction limited is rotationally symmetric, with a uniform brightness of the halo, deviations denote changes in shape and brightness of the image.

H2. Area of the halo image
H3. Brightness of the halo image
H4. Brightness of the delta image
H5. RMS Contrast of the halo image
H6. RMS Contrast of the delta image The optics of the cornea can be expressed in a variety of ways, including as follows:

O1. Wavefront aberration: RMS of the higher order aberrations, based on the Zernike coefficients over a 4-mm pupil (HOA)

O2. Wavefront aberration: RMS of the higher order aberrations, including the astigmatism terms, based on the Zernike coefficients over a 4-mm pupil (HOAA)

O3. Wavefront aberration: RMS of the asymmetrical higher order aberrations, including the astigmatism terms, based on the Zernike coefficients over a 4-mm pupil (AHOAA)

O4. Wavefront aberration: Coma, based on the Zernike coefficients over a 4-mm pupil (HOA)

O5. Wavefront aberration: Astigmatism, based on the Zernike coefficients over a 4-mm pupil (HOA)

O6. Wavefront aberration: Coma multiplied by Astigmatism, based on the Zernike coefficients over a 4-mm pupil (HOA)

O7. MTF Volume
O8. Area under the radial MTF curve

It should be understood that metrics have been derived from the halo images, and many other metrics can be derived, as known by those skilled in the art. The central theme is that the metrics are based on a retinal image of an extended object. In this example, the extended object is the headlight of a car.

Similarly, it should be understood that metrics have been derived from the optics of the eye, and many other metrics can be derived, as known by those skilled in the art. The central theme is that the metrics are based on the optics of the eye. In this example, the optics are described by corneal wavefront aberrations. The optics may further include aberrations caused by the internal optics of the eye, including those caused by the posterior cornea, and IOL misalignments.

Tables 1 and 2 show the results of single variable linear regression between the metrics of the bother of halo images and the metrics of the optics of the eye. Table 1 shows the P-values of least squares linear regression between the H- and O metrics. Table 2 shows the regression coefficient $R^2$. These results show that the patient inconvenience from halo images is significantly correlated with the optical characteristics of the eye.

TABLE 1

|    | H1    | H2    | H3    | H4   | H5    | H6    |
|----|-------|-------|-------|------|-------|-------|
| O1 | 4E−11 | 0.03  | 1E−05 | 0.18 | 3E−06 | 9E−12 |
| O2 | 4E−09 | 4E−03 | 1E−07 | 0.27 | 3E−08 | 2E−12 |
| O3 | 7E−11 | 0.04  | 2E−06 | 0.34 | 3E−07 | 2E−13 |
| O4 | 1E−15 | 0.86  | 2E−02 | 0.24 | 4E−03 | 4E−10 |
| O5 | 1E−03 | 2E−03 | 7E−07 | 0.62 | 5E−07 | 2E−06 |
| O6 | 2E−11 | 0.02  | 4E−07 | 0.34 | 3E−08 | 2E−15 |
| O7 | 2E−16 | 0.72  | 2E−03 | 0.10 | 1E−04 | 3E−15 |
| O8 | 3E−17 | 0.18  | 6E−06 | 0.02 | 2E−07 | 5E−21 |

TABLE 2

|    | H1   | H2   | H3   | H4   | H5   | H6   |
|----|------|------|------|------|------|------|
| O1 | 0.63 | 0.11 | 0.36 | 0.04 | 0.39 | 0.66 |
| O2 | 0.55 | 0.17 | 0.48 | 0.03 | 0.51 | 0.68 |
| O3 | 0.62 | 0.09 | 0.40 | 0.02 | 0.45 | 0.71 |
| O4 | 0.77 | 0.00 | 0.11 | 0.03 | 0.17 | 0.59 |
| O5 | 0.21 | 0.20 | 0.43 | 0.01 | 0.44 | 0.40 |
| O6 | 0.64 | 0.11 | 0.45 | 0.02 | 0.51 | 0.77 |
| O7 | 0.79 | 0.00 | 0.21 | 0.06 | 0.28 | 0.76 |
| O8 | 0.81 | 0.04 | 0.38 | 0.12 | 0.46 | 0.87 |

The above analysis demonstrates that the characteristics of the halo of multifocal IOLs are strongly influenced by ocular aberrations. In a preferred embodiment, the preoperative corneal aberrations of a patient are measured. If the pre-operative corneal aberrations exceed a certain threshold with respect to halo tolerance, then this can be a contraindication for implantation of a multifocal IOL.

The corneal aberrations can also be used to determine the type of multifocal IOL to be implanted, for example an aberration inducing or correcting IOL. Optimization may include modifying the design of the ophthalmic lens to change the shape and intensity profile in order to minimize halo inconvenience as further discussed below. It may be that specific shapes/intensity of a halo are less disturbing than the symmetrical homogenous intensity halo of a schematic eye. The IOL design can be optimized for a group of patients, e.g. the general cataract population of for a specific patient as detailed further below.

Additionally, the add power and light distribution for a diffractive multifocal IOL may be modified based on the corneal aberrations. For example, if a severe halo is expected based on corneal aberration analysis, then, in order to mitigate the inconvenience from halos, a multifocal IOL with a far-dominant light distribution may be chosen. For the same reason a multifocal IOL with a low add power may be chosen.

With reference to FIG. 3, preferred embodiments include utilizing corneal aberration data (which may include metrics based on corneal aberrations) in a computer-based eye model wherein retinal images of extended light sources are simulated. This could be performed via ray tracing using general purpose optical design software (e.g. Code V, Zemax, OSLO). The corneal shape may be part of the model eye. A multifocal intraocular lens is then appropriately positioned in the model. From this model eye, the point spread function (PSF) is calculated for a point source at the chosen vision condition, e.g. for distance vision. Subsequently, the PSF is convolved with an extended light source. Typically, the extended light source represents the headlight of a car. The convolved image represents a retinal light intensity profile of the extended light source, and reveals the size, shape and intensity of the halo.

This profile may then be compared to a reference halo, or set of reference halos, which demonstrates an acceptable dysphotopsia profile. The reference halos may be created by any of the following ways: by comparing the simulated halos from a group of multifocal IOL patients with their reported discomfort caused by halos; by displaying simulated images to a reference group and ranking the images based on expected discomfort; by measuring optical and visual performance of a reference group of multifocal IOL patients; or by having a reference group participate in a vision simulator experiment, in which the aberrations in the patient's eye are varied, while the visual performance is being tested. Once a (set of) reference halo(s) is created, the simulated halo may be compared to the reference halo. Based on this comparison, a decision may be made whether or not to (1) implant the multifocal IOL, (2) choose which IOL design to implant, (3) further optimize an IOL design, and/or (4) in the case of laser treatment decide on the treatment profile. In any case, the comparison between the simulated halo and reference halo optimizes the treatment in terms of mitigating the bother from halos.

Figure 5:
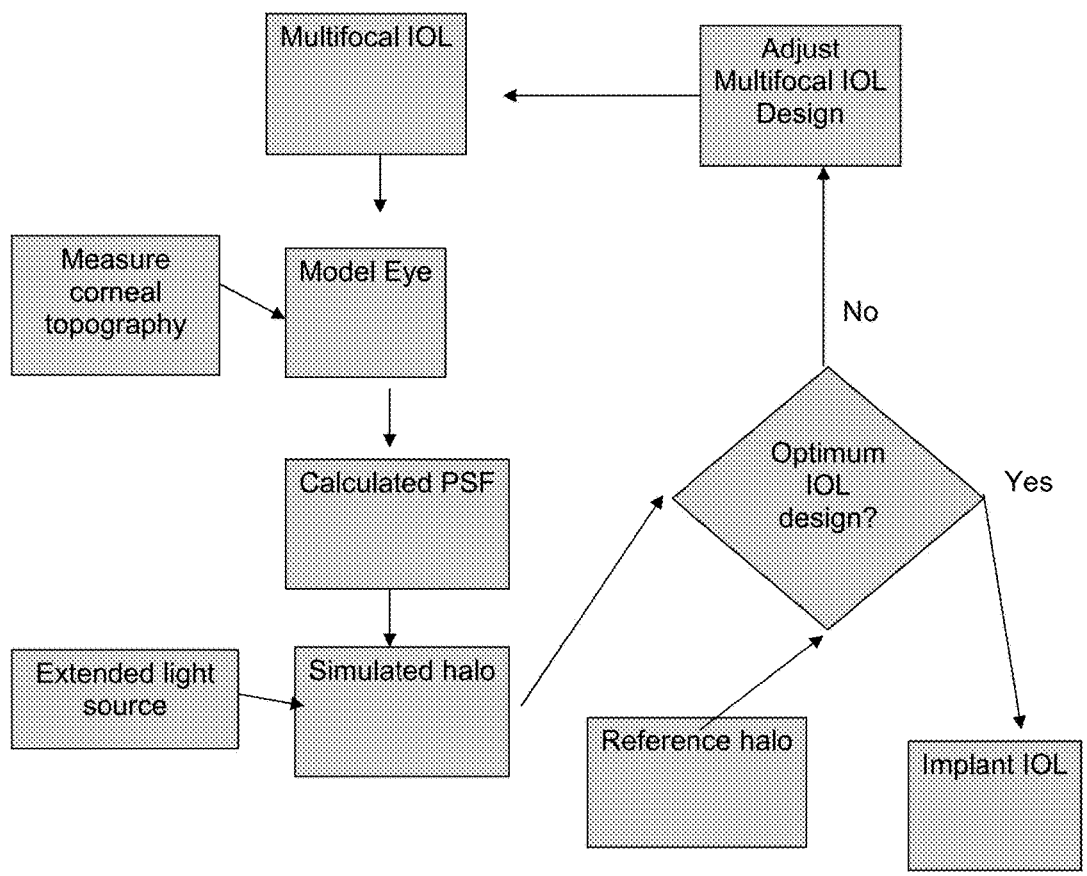
FIG. 5 is a flow diagram illustrating a method for optimizing an ophthalmic lens in accordance with the present invention.

FIG. 5 is a flow diagram illustrating another preferred embodiment wherein the preoperative corneal aberrations of a patient are measured and then simulated halo images calculated for these aberrations, with the multifocal IOL. The halo size, shape and intensity of the simulated images are then compared to a reference halo demonstrating acceptable dysphotopsia. Based on this information, the IOL aberration profile can be tailored so as to result in reduced or minimal bother from halo, specifically when combined with the patient's corneal aberration profile. For example, if the corneal aberrations include large amounts of coma and trefoil that produce a large and intense halo, an IOL could be designed that compensates for the corneal coma and trefoil, and thus, reduces or minimizes the halo. In comparison, spherical aberration has little effect on the halo appearance. This means that spherical aberration can be corrected or induced without (much) consequences for the bother from halos.

When the optical aberrations of the eye are expressed in terms of MTF Volume or area under the MTF curve, the correlation between halo appearance appears very strong. As the MTF Volume or the area under the MTF curve increases, less bother from halo is expected.

Clinically, it may happen that (for some patient or group of patients) a homogeneous and circular halo is not the optimal shape. In that case, the desired halo is not the halo as obtained with an aberration free eye, as used in the above example. However, the desired halo can be obtained by designing an IOL that introduces asymmetrical aberrations, such as coma, in order to match the desired halo.

In another preferred method an optimal aberration is determined using a vision simulator. The patient's natural aberrations are compensated by the instrument and a predetermined set of aberrations is induced. The patient looks at a scene, e.g. a night-driving scene, or a scene street lights, and then several sets of predetermined aberrations may be compared. The patient can then select the best scene (least disturbing halos). Alternatively, the patient can manipulate the magnitude and type of aberrations manually. Or, a set of sample images may be presented to the patient which represent the simulated scenes with different halo types. The patient can then select the best scene, and the appropriate IOL may be implanted or optimized and then implanted.

Laser ablation procedures can remove a targeted amount stroma of a cornea to change a cornea's contour and adjust for aberrations. In known systems, a laser beam often comprises a series of discrete pulses of laser light energy, with a total shape and amount of tissue removed being determined by a shape, size, location, and/or number of laser energy pulses impinging on a cornea.

Figure 6A:
FIGS. 6a and 6b are examples of halo size, shape and intensity in accordance with the present invention.

In a specific example, the corneal topography of a multifocal IOL patient was measured, and the corneal aberrations are calculated, as described above. The corneal aberrations, for a 6-mm corneal aperture are listed in table 3. The Zernike terms listed are shown in micrometers. A computer model of the patient's eye was made, and a multifocal lens inserted into the model eye. Using ray tracing, a PSF was calculated from the eye model, and the PSF was convolved with an extended light source. The result was a simulated halo, as shown in FIG. 6A. The size of this halo may be influenced by adjusting the corneal aberrations using laser vision correction.

Figure 6B:
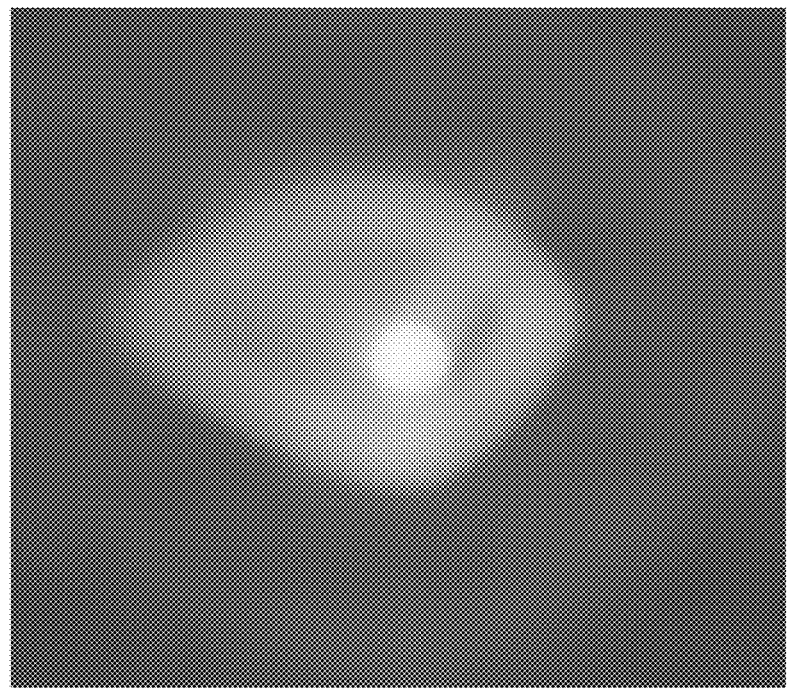

As an example, the same calculation was carried out using corneal aberrations as shown in table 4. Again, a computer model of the eye was made, now having the adjusted corneal aberrations, and the multifocal intraocular lens. The PSF was calculated, and the PSF was convolved with an extended light source. This resulted in a simulated halo, as shown in FIG. 6B. This example shows that the size, shape, and light intensities of the halo are influenced by the corneal aberrations. A corneal laser vision correction may then be used to change the corneal aberrations listed in table 3, into those listed in table 4.

TABLE 3

| Zernike term | Value |
| --- | --- |
| Z0 | −1.19900 |
| Z1 | −0.00700 |
| Z2 | 0.00550 |
| Z3 | 0.00058 |
| Z4 | 0.38743 |
| Z5 | 0.60012 |
| Z6 | 0.84004 |
| Z7 | −0.36840 |
| Z8 | 0.50803 |
| Z9 | 0.63816 |
| Z10 | 0.09440 |
| Z11 | 0.08633 |
| Z12 | 0.17582 |
| Z13 | −0.01241 |
| Z14 | 0.00520 |
| Z15 | −0.02003 |
| Z16 | 0.28460 |
| Z17 | 0.00506 |

TABLE 4

| Zernike term | Value |
| --- | --- |
| Z0 | 0.87200 |
| Z1 | 0.03200 |
| Z2 | 0.02350 |
| Z3 | −0.03868 |
| Z4 | 0.40131 |
| Z5 | 0.01388 |
| Z6 | 0.36911 |
| Z7 | 0.32138 |
| Z8 | −0.42977 |
| Z9 | 0.11208 |
| Z10 | 0.20435 |
| Z11 | 0.14736 |
| Z12 | 0.00632 |
| Z13 | −0.00173 |
| Z14 | −0.00115 |
| Z15 | −0.00756 |
| Z16 | 0.22073 |
| Z17 | −0.03131 |

Thus, a preferred embodiment, involves the following steps: measuring the preoperative corneal aberrations of the multifocal IOL patient; calculating a simulated halo image for these aberrations, with the multifocal IOL; determining the halo size, shape and intensity; having a reference halo which demonstrates acceptable dysphotopsia; optimizing the laser vision correction in order to achieve a minimal halo; applying the laser vision correction to the patient's cornea.

Another preferred embodiment, involves: measuring the preoperative corneal aberrations of the multifocal IOL patient; using a vision simulator to measure the patient's visual performance (e.g. halo size, shape and intensity; discomfort, contrast vision, visual acuity), while varying the patient's corneal aberration; based on the test, determining the optimal corneal aberration as to optimize the visual performance; applying a laser vision correction to generate the optimal corneal aberration onto the patient's cornea.

In another preferred method, after a multifocal IOL is implanted, one may measure corneal aberrations, e.g. by mathematically characterizing the corneal aberrations of the patient, using a method described above. Then a simulated halo image for these aberrations with the multifocal IOL may be calculated in order to determine the halo size, shape and intensity, as detailed previously. This simulated halo may then be compared to a reference halo which demonstrates acceptable dysphotopsia. If the simulated halo is significantly worse than the reference halo, the halo is predominantly caused by the corneal aberrations. Alternatively, a determination of whether the halo inconvenience results from corneal aberrations or the multifocal IOL may be based on experience of the relationship between patient complaints and ocular aberrations. This may be achieved by gathering information from patient files, and correlating the corneal data (corneal wavefront aberrations, calculated from corneal topography), with patient complaints referring to halos.

Minimizing halos may then be achieved by modifying the ocular aberrations through laser vision correction, with the optimal aberrations for the patient being determined using a vision simulator of sample images, or as otherwise detailed herein. Alternatively, an adjustable IOL may be implanted and then the aberrations changed after implantation. Or, an add-on (piggyback) IOL may be placed in front of the multifocal IOL. It is also envisioned that the multifocal IOL can be exchanged with a more appropriate design, or a corneal implant may be used and then the aberrations changed after the corneal implant is in place.

Another preferred embodiment, involves the following steps: optimizing a corneal correction (e.g. presby-lasik), the simulated halo image being one of the optimization parameters; applying the presby-laser vision correction to the patient's cornea. Prior to optimizing a corneal correction, one may measure the corneal aberrations of a patient suffering discomfort or reduced visual performance. It is envisioned that either the aberration profile can be optimized such that the halo will have minimal visual disturbances, or the aberration profile can be optimized such that the risk of severe visual disturbances is minimized.

An exemplary ophthalmic lens would include an anterior surface and an opposing posterior surface wherein at least one of the surfaces of the ophthalmic lens is characterized by an equation including a first coefficient configured to compensate for a corneal aberration in order to shape the halo and intensity profile in order to minimize bother from the halo.

Although the invention has been described and pictured in an exemplary form with a certain degree of particularity, it is understood that the present disclosure of the exemplary form has been made by way of example, and that numerous changes in the details of construction and combination and arrangement of parts and steps may be made without departing from the spirit and scope of the invention.

The invention claimed is:

1. A method comprising steps of:
obtaining corneal aberration data by measuring corneal aberrations of a patient's eye having a halo and having a multifocal intraocular lens implanted therein;
utilizing the corneal aberration data in a first eye model to calculate a simulated halo image, and wherein the first eye model is further comprised of a multifocal intraocular lens;
providing a reference halo or a set of reference halos produced from a second eye model having the multifocal intraocular lens of the first eye model and having corneal aberrations that are different than the corneal aberrations of the patient's eye or having no corneal aberrations;
comparing the simulated halo image to the reference halo or the set of reference halos;
determining, based on the comparison of the simulated halo image to the reference halo or the set of reference halos, whether the halo results from the corneal aberrations of the patient's eye; and
determining a laser vision correction to be applied to the patient to modify the corneal aberrations of the patient's eye to reduce the halo, the laser vision correction being determined based on the comparison of the simulated halo image to the reference halo or the set of reference halos.

2. The method of claim 1, wherein the reference halo or the set of reference halos demonstrate dysphotopsia.

3. The method of claim 1, wherein calculating the simulated halo image includes determining a halo size, a halo shape, and a halo intensity.

4. The method of claim 1, further comprising a step of applying the determined laser vision correction to the patient's eye.

5. The method of claim 1, further comprising utilizing an extended light source to calculate the simulated halo image.

6. The method of claim 5, wherein calculating the simulated halo image includes calculating a point spread function from the first eye model and convolving the point spread function with the extended light source.

7. The method of claim 1, wherein the first eye model is of the patient's eye.

8. The method of claim 1, further comprising a step of producing the reference halo or the set of reference halos.

9. The method of claim 1, wherein the step of determining the laser vision correction includes determining the laser vision correction that will minimize the halo.

* * * * *